United States Patent [19]

Searle et al.

[11] Patent Number: 5,597,933

[45] Date of Patent: Jan. 28, 1997

[54] PROCESS FOR THE PREPARATION OF N-ACETYL NEURAMINIC ACID DERIVATIVES

[75] Inventors: Andrew D. Searle, Stevenage; Christopher Williamson, Dartford, both of Great Britian

[73] Assignee: Biota Scientific Management Pty. Ltd., Victoria, Australia

[21] Appl. No.: 549,820

[22] PCT Filed: Jun. 15, 1994

[86] PCT No.: PCT/EP94/01940

§ 371 Date: Mar. 8, 1996

§ 102(e) Date: Mar. 8, 1996

[87] PCT Pub. No.: WO95/00503

PCT Pub. Date: Jan. 5, 1995

[30] Foreign Application Priority Data

Jun. 17, 1993 [GB] United Kingdom ............... 9312531

[51] Int. Cl.[6] .................................................. C07D 309/28
[52] U.S. Cl. .................................................. 549/424
[58] Field of Search ........................................... 549/424

[56] References Cited

FOREIGN PATENT DOCUMENTS

WO93/12105  6/1993  WIPO .

OTHER PUBLICATIONS

E. Schreiner et al., "Synthesis of Some 2,3–Didehydro–2–deoxysialic Acids Structurally Varied at C–4 and their Behavior towards Sialidase from *Vibrio cholerae*", Liebigs Annalen der Chemie, vol. 1991, No. 2, Feb. 1991, pp. 129–134.

*Primary Examiner*—Robert W. Ramsuer
*Assistant Examiner*—Laura L. Stockton
*Attorney, Agent, or Firm*— Foley & Lardner

[57] ABSTRACT

The invention provides a method for the preparation of the compound of formula(I)

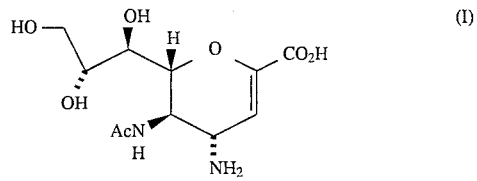

which comprises catalytic hydrogenolysis of a compound of formula (II)

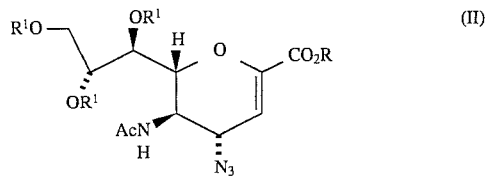

(wherein R is H or a $C_{1-4}$alkyl group and $R^1$ is H or a hydroxyl protecting group for example an acyl group such as acetyl) in aqueous formic acid followed, where necessary, by hydrolysis.

16 Claims, No Drawings

PROCESS FOR THE PREPARATION OF N-ACETYL NEURAMINIC ACID DERIVATIVES

This application is a 371 of PCT/EP94/01940 filed Jun. 15, 1994.

The present invention relates to a process for the preparation of derivatives of N-acetyl neuraminic acid. More particularly the invention relates to a process for the preparation of 5-acetamido-4-amino-2,3,4,5-tetradeoxy-D-glycero-D-galacto-non-2-enopyranosonic acid (the 4-amino analogue of DANA; also known as 5-(acetylamino)-4-amino-2,6-anhydro-3,4,5-trideoxy-D-glycero-D-galacto-non-2-enonic acid).

Schreiner et. al. Ann. Chem 1991, 129–134 describe the preparation of the 4-amino analogue of DANA from the peracetylated methyl ester of sialic acid (peracetyl NANA methyl ester) by the route shown in Scheme 1.

PCT/AU91/00161 (publication no. WO91/16320) describes the preparation of a number of derivatives of 5-acetamido 2,3,5-trideoxy-D-glycero-D-galacto-non-2-enopyranosonic acid (2,3-dideoxy-2,3-didehydro-N- acetylneuraminic acid; DANA) including the 4-amino analogue of DANA from the peracetylated methyl ester of DANA by a method similar to that of Schreiner et. al. with the exception that the peracetylated compound (3a) was reduced prior to deacetylation. The method is shown in Scheme 2.

Our copending application no. PCT/EP92/02904, publication no. WO 93/12105, published Jun. 24, 1993, describes a process for the preparation of 4-amino DANA from the corresponding peracetyl-4-azido analogue by catalytic hydrogenation using gaseous hydrogen.

We have now found that the yield and purity of 4-amino DANA can be improved by modification of the conversion of peracetyl 4-azido DANA to 4-amino DANA described in PCT/EP92/02904.

The invention thus provides a method for the preparation of the compound of formula (I)

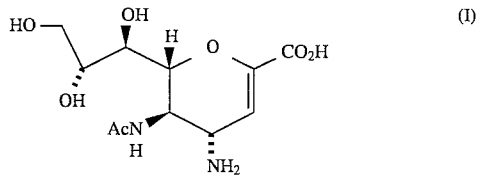

which comprises catalytic hydrogenolysis of a compound of formula (II)

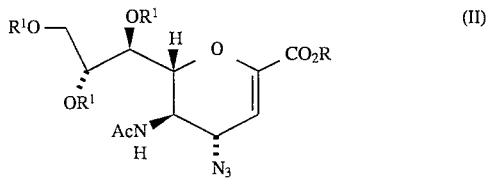

(wherein R is H or a $C_{1-4}$ alkyl group and $R^1$ is H or a hydroxyl protecting group for example an acyl group such as acetyl) in aqueous formic acid followed, where necessary, by hydrolysis.

By aqueous formic acid is meant a solution of formic acid in water or a mixture of water and any compatible organic solvent miscible with water. Preferably the solvent is water. Formic acid is conveniently present in an amount of 1–4 molar equivalents, for example about 2 molar equivalents of the compound of formula (II).

The formic acid acts as the source of hydrogen for the hydrogenolysis. It will be appreciated by those skilled in the art that the hydrogenolysis of the compound of formula (I) results in the liberation of nitrogen gas; it is thus advantageous to employ formic acid rather than hydrogen gas as the source of hydrogen.

The catalytic reduction may be effected with any suitable catalyst. In one preferred embodiment the catalyst is a palladium catalyst but in particular a poisoned palladium catalyst. A preferred poisoned palladium catalyst is a Pd catalyst poisoned with lead for example a Lindlar Catalyst. A particularly preferred catalyst comprises 5% palladium on a suitable support such as barium sulphate or, preferably, calcium carbonate, and 3 to 7% lead by weight of catalyst, such as 4 to 6% lead, more preferably 5% lead.

In an alterative preferred embodiment the catalyst is an unpoisoned catalyst, in particular, a palladium catalyst, for example palladium on charcoal.

The reduction is conveniently carried out at 0°–50° C., preferably at 20°–30° C.

In a preferred aspect of the invention the compound of formula (II) is deprotected, that is to say that R and $R^1$ are both hydrogen. The compound of formula (II) wherein R and $R^1$ are both hydrogen may be obtained by hydrolysis of the corresponding compound of formula (II) wherein R is a $C_{1-4}$ alkyl group and $R^1$ is a hydroxyl protecting group such as acetyl. The hydrolysis may be effected with any suitable inorganic or organic base. Preferably an organic base such as triethylamine or, particularly, 1,8-diazabicylo [5.4.0]undec-7-ene (DBU) is employed. Water or a mixture of water and any compatible organic solvent miscible with water is conveniently employed as the solvent. Preferably water is used. The reaction is conveniently carried out at ambient temperature. Conveniently at least 5 molar equivalents of base will be employed; alternatively a catalytic quantity of base may be employed where trans-esterification is used by incorporation of an alcohol, eg methanol, in the solvent mixture.

To facilitate isolation of the compound of formula (I), the pH of the reaction mixture is preferably optimised. Optimal pH for the isolation of the compound of formula (I) is in the range of 3 to 9, preferably 5 to 8, more preferably about 6.5. Adjustment to optimal pH may suitably be effected by addition of an acid, such as an organic acid, for example formic acid, or a base, such as an organic base, for example 1,8-diazabicyclo[5.4.0]undec-7-enem (DBU), as appropriate.

The compound of formula (I) may be isolated by any convenient method known in the art. However, the compound of formula (I) is preferably obtained by crystallisation. By this means 4-amino DANA is readily obtained substantially free of impurities.

Crystallisation can be induced by treating an aqueous solution of 4-amino DANA with an antisolvent, for example iso-propanol, at a temperature of from 10°–80 ° C., for example 25°–70° C. such as about 60° C.

The 4-amino analogue of DANA is a potent inhibitor of influenza virus both in vitro and in vivo and is thus useful in the treatment of viral infections such as influenza. (see for example WO91/16320).

The 4-amino analogue of DANA is also of use as an intermediate in the synthesis of other DANA derivatives which are inhibitors of influenza virus (see for example WO91/16320).

The invention is illustrated by the following non-limiting examples, All temperatures are in °C.

EXAMPLE 1

Methyl 5-acetamido-7,8,9-tri-O-acetyl-4-azido-2,3,4,5-tetradeoxy-D-glycero-D-galacto-non-2-enopyranosonate as its monohydrate, (20 g) was suspended in water (40 ml) and chilled with stirring to 10°. 1,8-Diazabicyclo[5,4,0]undec-7-ene (31.5 ml) was added over 20 minutes. The mixture was then stirred at 20° C. for 1.5 h, giving a clear solution.

Lindlar catalyst (1 g), then formic acid (3.2 ml) were added and the mixture stirred at 20° for 16 h. Filter aid (1 g) was added, then reaction mixture filtered to remove the catalyst. The spent catalyst bed was washed with water (3×0.67ml).

The filtrate and washings were combined and formic acid was added till a pH of 6.5 was reached. The resulting solution was heated to 60° and the product was crystallised by adding iso-propyl alcohol (400 ml) in portions.

The resulting crystalline slurry was cooled to 5° overnight, then filtered, and the product washed with iso-propyl alcohol (2×40 ml), then dried in vacuo at 40° for 16 h, to give the 4-amino analogue of DANA (12.25 g) as a trihydrate.

N.M.R. ($D_2O$)5.62 (1H,d,2); 4.40–4.25(2H,m); 4.18 (1 H,m);4.05–3.50 (4H,m); 2.08 (3H,s)

I.R. (Nujol) 3526, 3477, 3368, 3179 (HO,NH); 1675 (CO, amide), 1601 cm$^{-1}$ (CO, $CO_2H$).

EXAMPLE 2

A solution of Methyl 5-acetamido-7,8,9-tri-O-acetyl-4-azido-2,3,4,5-tetradeoxy-D-glycero-D-galacto-non-2-enopyranosonate as its monohydrate, (2 g) in water (6 ml) and methanol (14 ml) was treated with triethylamine (1.17 ml) and 1,8-diazabicyclo[5.4.0]undec-7-ene (1.89 ml). After stirring the resulting solution for 1.2 h at 20°, 10% palladium on activated carbon catalyst (0.2 g) and formic acid (0.32 ml) were added. The mixture was stirred under nitrogen at 20° for 18 h, then filter aid (0.2 g) added.

The reaction mixture was filtered to remove the catalyst, then the spent catalyst bed was washed with water (2×4ml). The filtrate and washings were combined and concentrated to 16 ml in vacuo. The resulting solution was heated to 60° and the product crystallised by adding iso-propyl alcohol (80 ml) in portions.

The resulting crystalline slurry was cooled to ambient temperature, then filtered, and the product washed with iso-propyl alcohol (2×4 ml), then dried in vacuo at 40°, to give the 4-amino analogue of DANA (0.63 g), identical to the product of Example 1.

EXAMPLE 3

A solution of Methyl 5-acetamido-7,8,9-tri-O-acetyl-4-azido-2,3,4,5-tetradeoxy-D-glycero-D-galacto-non-2-enopyranosonate as its monohydrate, (100 g) in water (150 ml) at about 10° was treated with 1,8-diazabicyclo[5.4.0]undec-7-ene (158 ml) and stirred at about 20° for ca. 1.5h, giving a solution. Lindlar catalyst (5 g) comprising 5% palladium on calcium carbonate and 5% lead was added, followed by formic acid (15.9 ml) whilst the temperature was kept below 30°. The mixture was maintained at 25°–30° for approximately 16 h. The catalyst was removed by filtration through a prepared filter-bed, which was then washed with water (2×50 ml).

The combined filtrate and washings were adjusted to pH6.5 by addition of formic acid (10 ml). The solution was stirred for 30 min, then re-acidified to pH6.5 by addition of a further few drops of formic acid. The solution was warmed to about 606 and diluted with isopropanol (800 ml), then allowed to crystallise. The mixture was reheated to 60° and further diluted with isopropanol (1200 ml). The resulting suspension was stirred for approximately 16 h, then cooled to about 5°. The solid was isolated by filtration, washed with isopropanol (2×200 ml) and vacuum dried at 40° to give the 4-amino analogue of DANA (62.4 g), identical to the product of Example 1.

Scheme 1

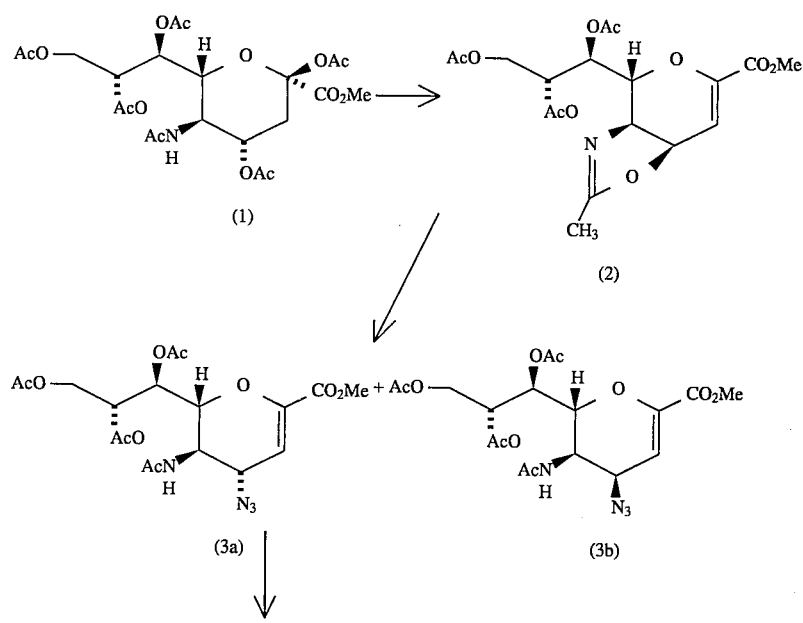

-continued
Scheme 1

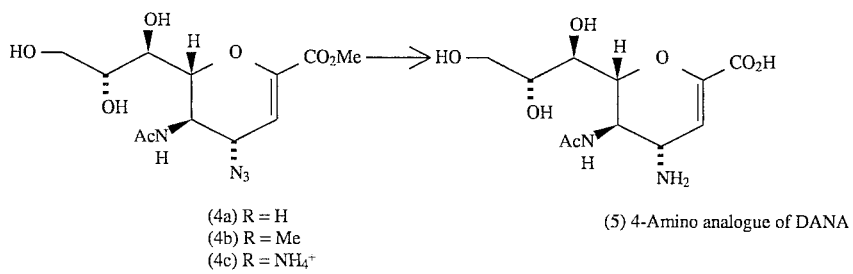

(4a) R = H
(4b) R = Me
(4c) R = NH$_4^+$ (5) 4-Amino analogue of DANA

Scheme 2

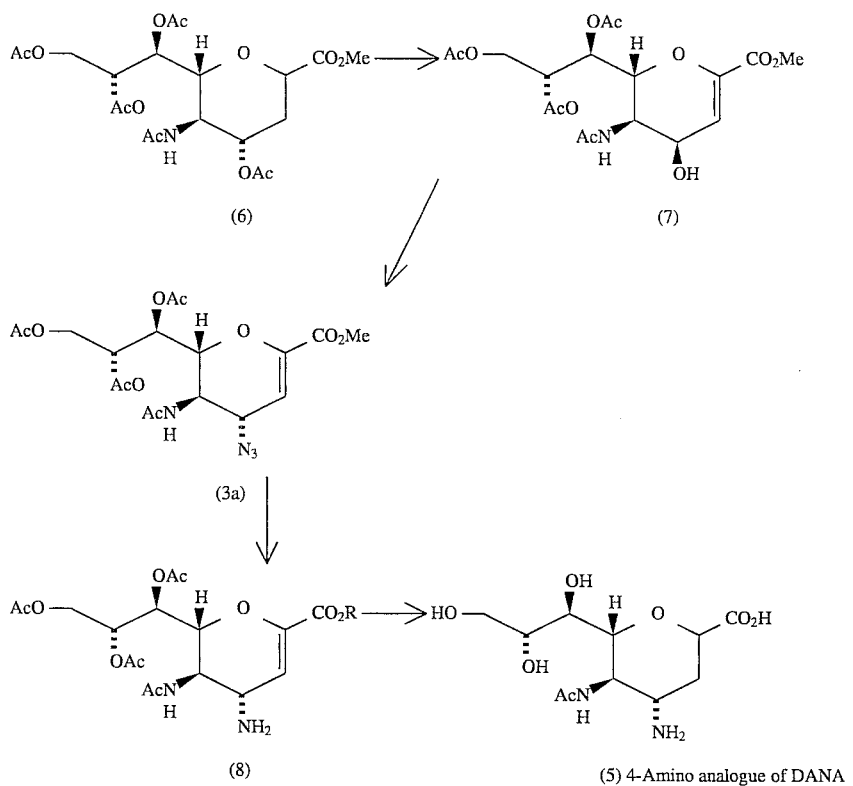

We claim:

1. A process for the preparation of a compound of formula (I)

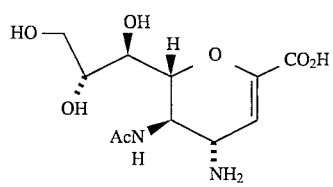

which comprises catalytic hydrogenolysis of a compound of formula (II)

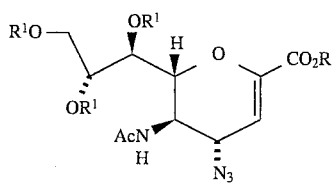

wherein R is H or $C_{1-4}$alkyl and $R^1$ is H or a hydroxyl protecting group, in aqueous formic acid.

2. A process as claimed in claim 1 wherein the catalyst is a palladium catalyst.

3. A process as claimed in claim 1 wherein the catalyst is a poisoned palladium catalyst.

4. A process as claimed in claim 1 wherein the catalyst is a palladium catalyst poisoned with lead.

5. A process as claimed in claim 1 wherein the catalyst is a Lindlar catalyst.

6. A process as claimed in claim 1 wherein the catalyst comprises 5% palladium on a support and 3 to 7% lead.

7. A process as claimed in claim 6 wherein the support is calcium carbonate.

8. A process as claimed in claim 6 wherein the lead content is 5%.

9. A process as claimed in claim 1 wherein the formic acid is present in an amount of 1–4 molar equivalents of the compound of formula (II).

10. A process as claimed in claim 9 wherein the formic acid is present in an amount of about 2 molar equivalents of the compound of formula (II).

11. A process as claimed in claim 1 which is carried out at a temperature of 0° to 50° C.

12. A process as claimed in claim 1 wherein in the compound of formula (II) at least one of R and $R^1$ is not hydrogen and wherein the product of reduction is subsequently hydrolysed.

13. A process as claimed in claim 12 wherein the hydrolysis is effected in aqueous medium.

14. A process as claimed in claim 12 wherein the hydrolysis is effected with a base selected from triethylamine and 1,8-diazabicyclo [5.4.0]undec -7-ene.

15. A process as claimed in claim 1 wherein the pH of the reaction mixture is adjusted to within the range of 3 to 9 prior to isolation of the compound of formula (I).

16. A process as claimed in claim 15 wherein the pH is adjusted to about 6.5.

* * * * *